US012419621B2

(12) United States Patent
Montenegro et al.

(10) Patent No.: US 12,419,621 B2
(45) Date of Patent: Sep. 23, 2025

(54) DEVICE, SYSTEMS, AND METHODS FOR GRASPING TISSUE AT A MUSCULAR LEVEL

(71) Applicant: Boston Scientific Scimed, Inc., Maple Grove, MN (US)

(72) Inventors: Esteban S. Montenegro, Heredia (CR); Jairo M. Vargas Mena, Heredia (CR); Gonzalo J. Saenz Villalobos, Alajuela (CR)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 121 days.

(21) Appl. No.: 17/404,574

(22) Filed: Aug. 17, 2021

(65) Prior Publication Data

US 2022/0183670 A1 Jun. 16, 2022

Related U.S. Application Data

(60) Provisional application No. 63/126,165, filed on Dec. 16, 2020.

(51) Int. Cl.
*A61B 17/00* (2006.01)
*A61B 17/29* (2006.01)

(52) U.S. Cl.
CPC ........ *A61B 17/00234* (2013.01); *A61B 17/29* (2013.01); *A61B 2017/00349* (2013.01); *A61B 2017/2926* (2013.01)

(58) Field of Classification Search
CPC .............. A61B 17/00234; A61B 17/29; A61B 2017/00349; A61B 2017/2926; A61B 2017/0641
See application file for complete search history.

(56) References Cited

U.S. PATENT DOCUMENTS 4,836,205 A * 6/1989 Barrett .................... A61B 17/29 606/144
2006/0025789 A1* 2/2006 Laufer ............... A61B 17/0686 606/153

(Continued)

FOREIGN PATENT DOCUMENTS

JP 2009502365 A 1/2009

OTHER PUBLICATIONS

International Search Report and Written Opinion for the International Patent Application No. PCT/US2021/046300, mailed Nov. 15, 2021, 15 pages.

*Primary Examiner* — Shaun L David
*Assistant Examiner* — Rachael L Geiger
(74) *Attorney, Agent, or Firm* — Seager, Tufte & Wickhem, LLP

(57) ABSTRACT

A tissue repair device, system, and method for grasping tissue, such as to repair the tissue (e.g., a defect in tissue), by anchoring a tissue-penetrating arm along a first location along the tissue, moving the anchored tissue-penetrating arm to a second location along the tissue, and grasping tissue at the second location with a tissue-grasping arm. The tissue-penetrating arm remains in a substantially axial straight configuration to facilitate tissue penetration. The tissue-grasping arm is movable towards and away from the tissue-penetrating arm to grasp tissue and hold the grasped tissue between the tissue-grasping arm and the tissue-penetrating arm. The tissue repair device may be left in place holding the tissue in the grasped configuration.

17 Claims, 6 Drawing Sheets

1003
1030
1020
1013
1000
1010
130
1011
100
1001
140
110
120

(56) References Cited

U.S. PATENT DOCUMENTS

| | | | | |
|---|---|---|---|---|
| 2007/0027464 | A1 | 2/2007 | Way et al. | |
| 2008/0077162 | A1* | 3/2008 | Domingo | A61B 17/0469 606/146 |
| 2011/0098730 | A1* | 4/2011 | Kelleher | A61B 17/1285 606/151 |
| 2014/0088616 | A1* | 3/2014 | Clerc | A61B 17/083 606/142 |
| 2016/0000433 | A1* | 1/2016 | Raybin | A61B 17/1227 606/145 |
| 2016/0051252 | A1* | 2/2016 | Smith | A61B 17/0466 606/232 |
| 2017/0319208 | A1* | 11/2017 | Smith | A61B 17/1227 |
| 2019/0053818 | A1* | 2/2019 | Nelson | A61B 17/282 |
| 2020/0093496 | A1 | 3/2020 | Ryan et al. | |

* cited by examiner

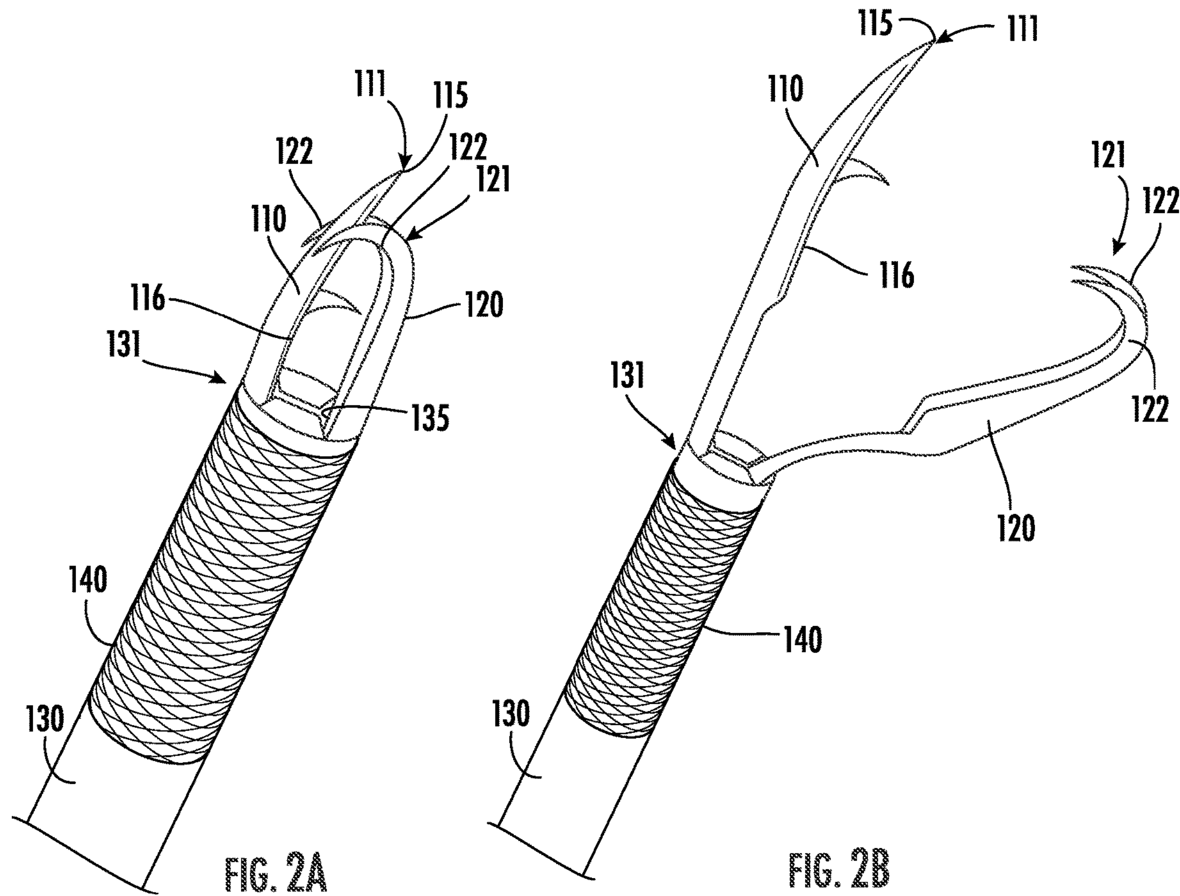
FIG. 2A
FIG. 2B
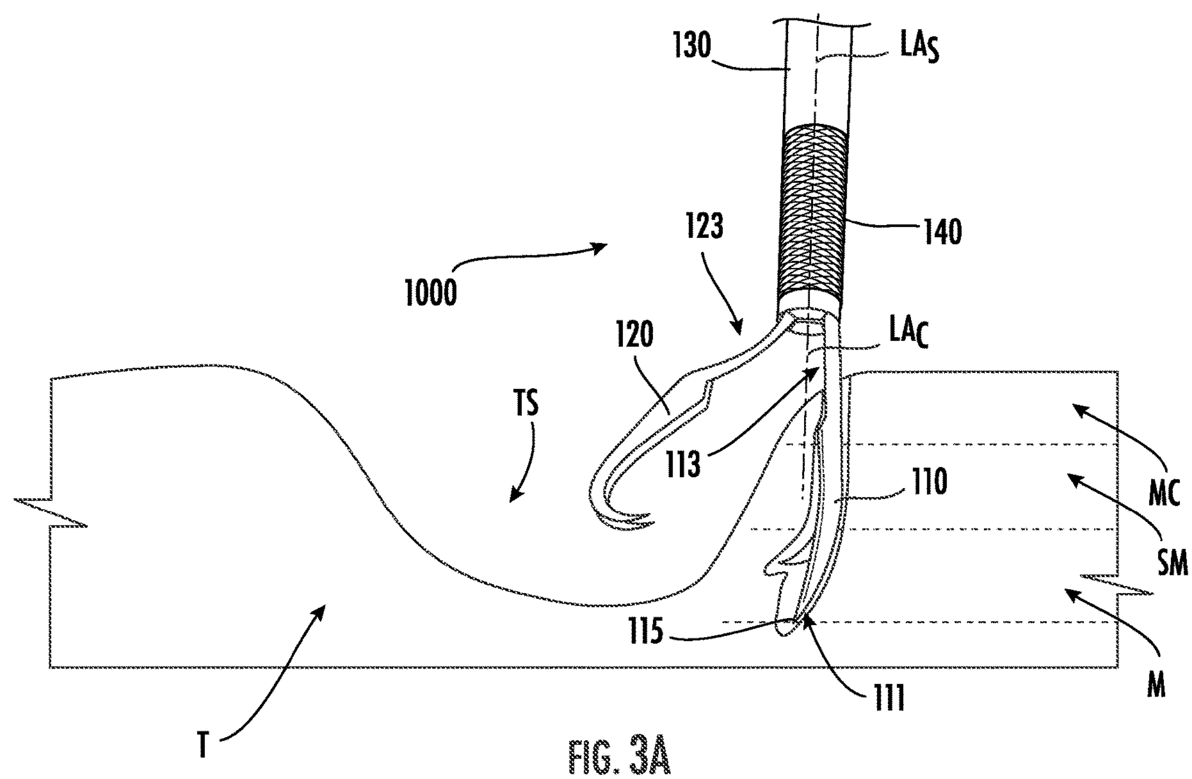
FIG. 3A

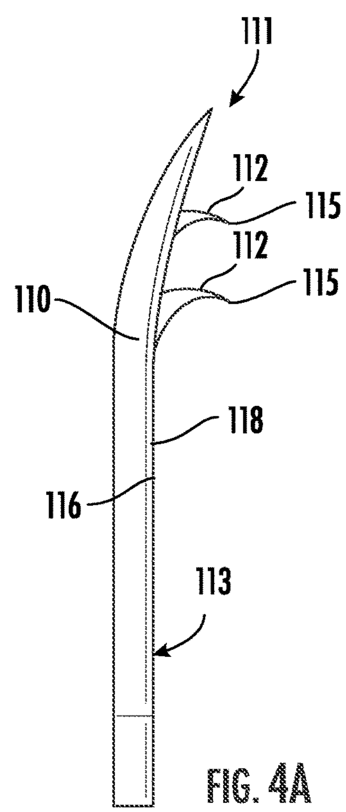
FIG. 4A
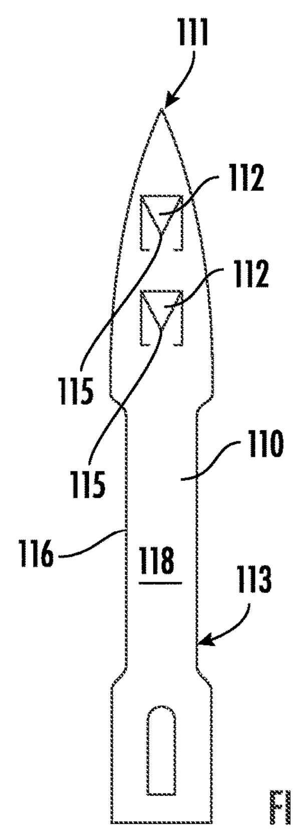
FIG. 4B
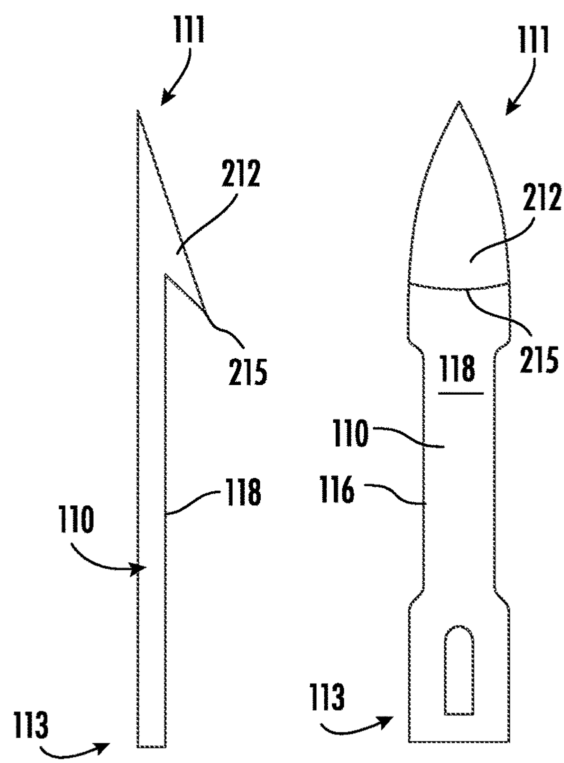
FIG. 5A
FIG. 5B
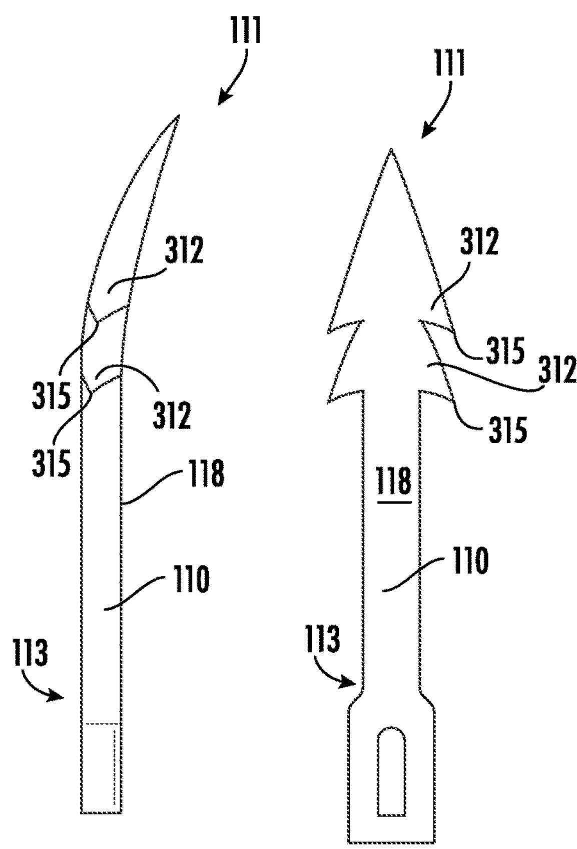
FIG. 6A
FIG. 6B

DEVICE, SYSTEMS, AND METHODS FOR GRASPING TISSUE AT A MUSCULAR LEVEL

PRIORITY

The present application is a non-provisional of, and claims the benefit of priority under 35 U.S.C. § 119 to U.S. Provisional Application Ser. No. 63/126,165, filed Dec. 16, 2020, the disclosure of which is hereby incorporated herein by reference in its entirety for all purposes.

FIELD

The present disclosure relates generally to devices, systems, and methods for grasping tissue at a muscular level. More particularly, the present disclosure relates to devices, system, and methods for repairing a muscular tissue wall.

BACKGROUND

Endoscopic and therapeutic procedures such as EMR (endoscopic mucosal resection) and ESD (endoscopic submucosal dissection) are often performed as treatment/prevention for several conditions inside the gastrointestinal track. These endoscopic procedures are often followed by a mechanical closure of the lesion using a hemostasis clip. Through-The-Scope clips (TTS) have been most widely preferred for repairing defects inside the GI tract because they are relatively easy to use. However, the TTS clips currently available in the market are designed to close defects at a superficial level, meaning at the mucosal and submucosal layers of the tissue. Some procedures, depending on the size and depth of the defect, require a deeper closure along the thickness, unto the muscular layer of the tissue. To achieve this, physicians often appeal to the use of other devices such as Over-The Scope-Clips (OTSC) due to their larger size and strength, beneficial to close defects at a deeper layer. Nevertheless, these devices generally are harder to use and do not provide as controlled actuation as the TTS clips.

Improved devices, systems, and methods for providing closure of tissue, such as defects in tissue, at a muscular layer would thus be welcome in the medical field.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a tissue repair device and associated system and method is capable of penetrating muscular tissue to repair or otherwise affect the muscular tissue.

In accordance with some aspects of the present disclosure, the tissue repair device includes a tubular component having a longitudinal axis and a lumen defined therein; and a tissue-penetrating arm and a tissue-grasping arm extendable from within the lumen of the tubular component to a position outside the lumen of the tubular component. The tissue-penetrating arm is maintained in a position substantially parallel to the tubular component longitudinal axis when extended to a position outside the tubular component lumen. The tissue-grasping arm is movable with respect to the tubular component longitudinal axis toward or away from the tissue-penetrating arm.

In some embodiments of a tissue repair device, the tissue-grasping arm is biased to move away from the tissue-penetrating arm when extended to a position outside the tubular component lumen, the tissue-penetrating arm and the tissue-grasping arm being in a closed configuration while within the tubular component lumen and in an open position when extended to a position outside the tubular component lumen.

In some embodiments of a tissue repair device, the tissue-penetrating arm includes a sharp edge or tip configured to penetrate into tissue. In addition or alternatively, the tissue-penetrating arm has a length sufficient to penetrate through mucosal, submucosal, and muscular layers of a small intestine without penetrating through the wall of the small intestine. In addition or alternatively, the tissue-grasping arm has a blunt distal end. In addition or alternatively, the tissue-grasping arm is configured to inhibit the depth to which the tissue-penetrating arm may penetrate into tissue. In addition or alternatively the tissue-penetrating arm includes a sharp distal end, and a tissue-penetrating hook positioned proximal to the sharp distal end. In some embodiments, the tissue-penetrating hook extends transverse to the tubular component longitudinal axis. In some embodiments, the tissue-penetrating hook is shaped and configured to retain tissue when the tissue-penetrating arm is moved laterally. In some embodiments, the tissue-grasping arm includes at least one tissue-grasping hook. In some embodiments, the tissue-grasping hook faces toward the tissue-penetrating arm. In some embodiments, the tissue-grasping hook includes a pair of tissue-grasping hooks, and the tissue-penetrating arm fits between the tissue-grasping hooks when the tissue-grasping arm is moved toward the tissue-penetrating arm. In some embodiments, the tissue-penetrating arm includes at least one hook shaped and configured to retain tissue when at least one of tissue-grasping arm or the tissue-penetrating arm is moved laterally.

In accordance with further aspects of the present disclosure, a tissue repair system includes a flexible elongate member having a lumen defined therein, and a longitudinal axis extending between a distal end of the flexible elongate member and a proximal end of the flexible elongate member; a pair of grasper arms which are shaped and configured differently from each other and are extendable from within the flexible elongate member lumen to a position outside the flexible elongate member lumen; a controller having a proximal end and a distal end, the controller distal end coupled to the grasper arms to move the grasper arms between a position within the flexible elongate member lumen and a position distally outside the flexible elongate member lumen; and a control handle coupled with the proximal ends of the flexible elongate member and the controller to control movement thereof.

In some embodiments of a tissue-repair system, the grasper arms include a tissue-penetrating arm which is maintained in a position substantially parallel to the flexible elongate member longitudinal axis when extended to outside the flexible elongate member lumen, and a tissue-grasping arm movable with respect to the flexible elongate member longitudinal axis toward or away from the tissue-penetrating arm. In some embodiments, the tissue-repair system further includes a capsule coupled to the distal end of the flexible elongate member and defining a lumen therethrough, the grasper arms movable between a closed configuration within the capsule and an open configuration outside the capsule. In some embodiments, the capsule is separable from the flexible elongate member with the grasper arms positioned therein in a closed position.

In accordance with further aspects of the present disclosure, a method of repairing tissue includes axially advancing a tissue-penetrating arm of a tissue repair device into tissue at a first location along a treatment site to be anchored into the tissue at the first location; moving the tissue-penetrating arm to a second location along the treatment site; grasping tissue at the second location with a tissue-grasping arm of the tissue repair device extending laterally away from the tissue-penetrating arm; and moving the tissue-grasping arm towards the tissue-penetrating arm to hold together the tissue at the first location and the tissue at the second location.

In some embodiments, the tissue-penetrating arm is maintained in a substantially straight configuration during the tissue repair method. In addition or alternatively, the tissue repair device includes a capsule surrounding proximal ends of the tissue-grasping arm and the tissue-penetrating arm, and is coupled with a controller configured and arranged to control movement of the tissue-penetrating arm and the tissue-grasping arm, the method further including detaching the capsule from the controller with the tissue-grasping arm and the tissue-penetrating arm within the capsule in a closed configuration grasping the tissue at the first location and the second location to close a tissue defect therebetween.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 2A is a perspective view of a tissue repair device formed in accordance with various principles of the present disclosure in a closed configuration.

FIG. 2B is a perspective view of a tissue repair device formed in accordance with various principles of the present disclosure in an open configuration.

FIGS. 3A, 3B, 3C, 3D, and 3E illustrate sequential positions of a tissue repair device formed in accordance with various principles of the present disclosure with respect to a tissue defect to be repaired in accordance with various principles of the present disclosure, with a flexible elongate member shown in phantom in FIG. 3E.

FIGS. 4A and 4B show an isolated side and front elevational view, respectively, of an alternate embodiment of a tissue-penetrating arm in accordance with various principles of the present disclosure.

FIGS. 5A and 5B show an isolated side and front elevational view, respectively, of an alternate embodiment of a tissue-penetrating arm in accordance with various principles of the present disclosure.

FIGS. 6A and 6B show an isolated side and front elevational view, respectively, of an alternate embodiment of a tissue-penetrating arm in accordance with various principles of the present disclosure.

DETAILED DESCRIPTION

Figure 1:
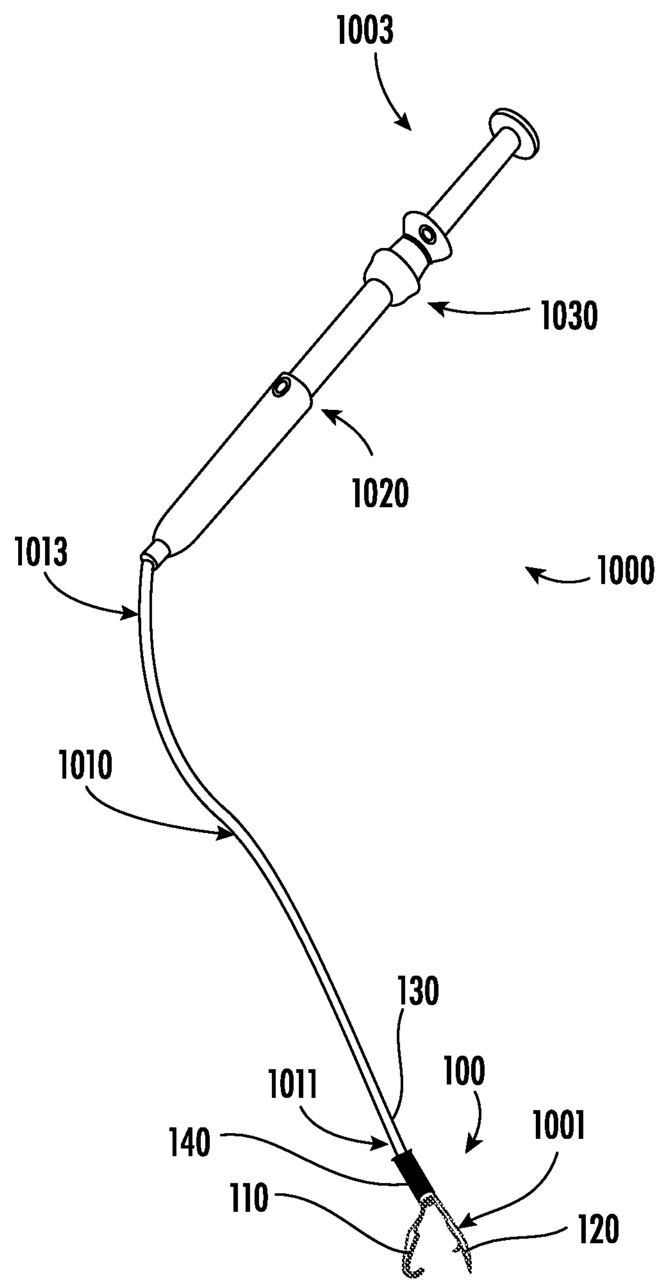
FIG. 1 is a perspective view of a tissue repair assembly formed in accordance with various principles of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, “proximal” refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and “distal” refers to the direction or location furthest from the user, such as when using the device (e.g., introducing the device into a patient, or during implantation, positioning, or delivery). “Longitudinal” means extending along the longer or larger dimension of an element. “Central” means at least generally bisecting a center point, and a “central axis” means, with respect to an opening, a line that at least generally bisects a center point of the opening, extending longitudinally along the length of the opening when the opening comprises, for example, a tubular element, a channel, a cavity, or a bore.

A tissue repair device configured to repair a tissue defect, such as at a muscular layer, and accompanying systems and methods are disclosed and described herein. It will be appreciated that reference to tissue repair is for the sake of convenience and without intent to limit, as further applications and uses of the devices, systems, and methods disclosed herein are within the scope and spirit of the present disclosure. Moreover, it will be appreciated that reference to tissue defect herein is for the sake of convenience and without intent to limit, and intended to refer to a site on tissue at which there is a cut, lesion, gap, break, fissure, incision, laceration, tear, perforation, fistula, stapling, etc., or other separation of tissue defining sides, edges, etc., of tissue along, around, surrounding, etc., the defect (in each separate listing of terms, the terms in such list may be used interchangeably herein without intent to limit).

In various embodiments as disclosed herein, a tissue repair device in accordance with various aspects of the present disclosure has at least two arms. One of the arms may be different in configuration from another arm, and thereby may perform or serve different functions. In some embodiments, one of the arms of a tissue repair device formed in accordance with various aspects of the present disclosure is configured to be a tissue-penetrating arm capable of penetrating tissue, such as intestinal tissue, into the muscular layer of the tissue (e.g., beyond the mucosal and submucosal layers such as of intestinal tissue). In some embodiments, the tissue-penetrating arm includes at least one sharp region, such as a sharp tip (e.g., distal end) and/or sharp longitudinal edge, to penetrate through layers of tissue, such as above a muscular layer of tissue, to reach the muscular tissue layer.

In some embodiments, the other arm of the tissue repair device is a tissue-grasping arm configured to engage and grasp (such terms being used herein for the sake of simplicity without intent to limit, and may be used interchangeably herein with such terms as grapple, grab, hold, clasp, clip, etc.) tissue and draw the tissue to the tissue-penetrating arm. The tissue-penetrating arm preferably may be sufficiently stabilized or seated or anchored in the tissue through which it penetrates to draw (such term being used interchangeably herein with such terms as bring, carry, etc., without intent to limit) tissue therewith as the tissue repair device is moved to a different position along the tissue defect at which the tissue-grasping arm may grasp a different portion of tissue in the region of (e.g., alongside or adjacent) the tissue defect. The tissue-grasping arm may then be moved relative to the tissue-penetrating arm to grasp tissue between the arms, such as to effect repair of the defect (e.g., to bring together the different portions of the tissue engaged by the tissue-penetrating arm and the tissue-grasping arm to close an opening in the tissue).

In some embodiments, the tissue-penetrating arm remains substantially stationary and is inhibited or prevented from moving (such as bending or pivoting) laterally from a longitudinal position substantially aligned with the longitudinal axis of a flexible elongate member carrying the tissue repair device. As such, the tissue-penetrating arm remains securely anchored within the tissue which it penetrates. In some embodiments, the tissue-grasping arm is flexible or pivotable to move (such term being used for the sake of convenience without intent to limit, and may be used interchangeably herein with terms such as expand or extend) relative to the tissue-penetrating arm. For instance, the tissue-grasping arm may be formed of a flexible material, such as stainless steel or a shape-memory material, to flex away from the tissue-penetrating arm, or may be pivotable so that it can pivot away from the tissue-penetrating arm. The tissue-grasping arm may be selectively moved away from the tissue-penetrating arm to engage tissue and then be brought closer to the tissue-penetrating arm to grasp tissue between the tissue-grasping arm and the tissue-penetrating arm.

A flexible elongate member (such as a shaft, a catheter, a sheath, a tube, or the like, such terms being used interchangeably herein without intent to limit) may carry the arms as well as additional devices to control operation of the arms, such as a controller. The flexible elongate member may be a tubular element with a lumen extending longitudinally therethrough, through which components of the system may be extended or delivered, though in some embodiments the flexible elongate member need not have a lumen therethrough. The controller may be a control wire or shaft or the like capable of extending through (e.g., through a lumen within) or along the flexible elongate member to maneuver (such term being used for the sake of convenience without intent to limit, and may be used interchangeably herein with terms such as manipulate, move, control, actuate, etc., including various conjugations thereof) the tissue repair device. The controller may extend from a distal end, at which the tissue repair device is carried, to a proximal end, at which a control handle or the like may be provided to effect actuation of the controller.

In various embodiments, the tissue repair device includes a capsule in which the arms of the tissue repair device may be movably housed, with the capsule coupled or mounted (such terms being used interchangeably herein without intent to limit) to the flexible elongate member. The capsule may be an integral part of the distal end of the flexible elongate member or may be a separate tubular component coupled thereto. The capsule may be separable (with the arms of the tissue repair device) from the flexible elongate member to leave the tissue repair device in place with the arms thereof holding tissue together to repair the defect.

Various embodiments of a tissue repair device and accompanying assembly and method will now be described with reference to examples illustrated in the accompanying drawings. Reference in this specification to “one embodiment,” “an embodiment,” “some embodiments”, “other embodiments”, etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

It will be appreciated that in the following description, elements or components similar among the various embodiments illustrated in the accompanying drawings are generally designated with the same reference numbers increased by 100 and redundant description is omitted. Common features are identified by common reference elements and, for the sake of brevity, the descriptions of the common features are generally not repeated. For purposes of clarity, not all components having the same reference number are numbered.

It should be understood that one or more of the features described with reference to one embodiment can be combined with one or more of the features of any of the other embodiments provided herein. That is, any of the features described herein can be mixed and matched to create hybrid designs, and such hybrid designs are within the scope of the present disclosure.

Turning now to the drawings, a tissue repair device 100 formed in accordance with various principles of the present disclosure is illustrated in FIG. 1. The tissue repair device 100 may be considered to be part of a tissue-repair system 1000 which includes a delivery device, such as a flexible elongate member 1010 with a distal end 1011 along or at which the tissue repair device 100 is delivered, and a proximal end 1013 coupled to a control handle 1020 or the like, by which the flexible elongate member 1010 may be maneuvered. It will be appreciated that the term flexible elongate member is used herein for the sake of convenience to refer to a delivery device in general and without intent to limit, and may be in the form of a catheter, sheath, tube, cannula, etc. In some embodiments, the flexible elongate member 1010 has a working channel therethrough via which a tissue-repair device controller 1030 (including a control element 1032 such as a control wire, as illustrated in FIG. 3E) is guided. In other embodiments (not illustrated), the tissue-repair device controller 1030 extends along but not through the flexible elongate member 1010. The tissue repair-device controller 1030 (shown schematically in phantom lines extending through the flexible elongate member 1010) operably extends (e.g., at least a component thereof, such as the control element 1032, extends) from the tissue repair device 100 at a distal end 1001 of the tissue-repair system 1000, to the proximal end 1003 of the tissue-repair system 1000 for access and manipulation by the user (e.g., medical professionals, such as physicians, technicians, endoscopists, etc., and/or automated system or otherwise) to control the tissue repair device 100. The control handle 1020, at the proximal end 1003 of the tissue-repair system 1000, may be associated with the tissue-repair device controller 1030 and/or a controller of the flexible elongate member 1010 (any controller known or heretofore known in the art and not illustrated as not necessary for a complete understanding of the tissue-repair device 100).

In accordance with one aspect of the present disclosure, the tissue repair device 100 includes a pair of grasper arms 110, 120 extending from a shaft 130, as illustrated in greater detail in FIGS. 2A and 2B, and FIGS. 3A-3E. The shaft 130 may be a distal portion of the flexible elongate member 1010. In some embodiments, the tissue repair device 100 includes a capsule 140 (a tubular element with a lumen defined therein) in which the grasper arms 110, 120 are movably housed. The capsule 140 may be coupled or mounted (such terms being used interchangeably herein without intent to limit) to the distal end 1011 of the flexible elongate member 1010 and may serve as the shaft 130.

The grasper arms 110, 120 are extendable from a closed configuration within a lumen 135 formed within the shaft 130, to an open configuration distally beyond the distal end 131 of the shaft 130. The tissue repair device 100 may extend in a closed configuration distally through the flexible elongate member 1010 for delivery to the treatment site TS (FIGS. 1 and 3A-3E). The grasper arms 110, 120 may be delivered in a closed configuration stored within the shaft lumen 135 and with a sufficiently low profile to move distally through the tissue-repair system 1000, such as through the flexible elongate member 1010. The tissue-repair device controller 1030 is actuatable (e.g., movable) to actuate the tissue repair device 100 to cause the grasper arms 110, 120 to move from a closed configuration, as illustrated in FIG. 2A, to an open configuration as illustrated in FIG. 2B. In some embodiments, the tissue-grasping arm 120 is biased or pivotable to move with respect to (such as away from) the tissue-penetrating arm 110, such as upon moving distally from within the confines of the shaft lumen 135, into an open configuration. In some embodiments, the tissue-grasping arm 120 is formed of a resilient flexible material (e.g., stainless steel), and may be formed of a shape memory material (e.g., an alloy, such as Nitinol). In some embodiments, the tissue-repair device controller 1030 is moved distally or proximally to actuate at least the tissue-grasping arm 120 to move to an open configuration or a to a closed configuration. However, other movements or control of the tissue repair device 100 are within the scope of the present disclosure, the particular movements not being critical to the broad principles of the present disclosure.

In accordance with various principles of the present disclosure, the tissue-penetrating arm 110 is substantially straight and substantially parallel to a capsule longitudinal axis $LA_C$ and a shaft longitudinal axis $LA_S$ and remains substantially straight once it extends distally from the shaft 130. Moreover, tissue-penetrating arm 110 is preferably sufficiently stiff and rigid to be able to be pushed distally (generally along the shaft longitudinal axis $LA_S$ and/or the capsule longitudinal axis $LA_C$) into tissue at a treatment site (e.g., a site with a tissue defect) without deflecting or bending. The tissue-penetrating arm 110 has a length and a sharp distal end 111 shaped and configured to be capable of penetrating through tissue, preferably through muscular tissue, such as a sharp distal tip 115. As such, the tissue-penetrating arm 110 may be considered a needle or spear of the tissue repair device 100. In some embodiments, the tissue-penetrating arm 110 may include a sharp longitudinal side edge 116 on one or both side edges (the narrow sides or edges of the tissue-penetrating arm 110, generally not facing the tissue-grasping arm 120) thereof. In some embodiments, the sharp edge may be in the form of one or more teeth. As such, the tissue-penetrating arm 110, in addition to being considered a needle or spear, may be considered a blade, the sharp longitudinal side edge 116 cutting through tissue as the tissue-penetrating arm 110 is axially extended towards the tissue. Because the tissue-penetrating arm 110 is substantially stiff and rigid, the tissue-penetrating arm 110 moves axially as the tissue repair device 100 is moved distally and transfers or transmits the axial force of the flexible elongate member 1010, shaft 130, and/or capsule 140 to the sharp distal end 111 to assist in penetrating the tissue. The length of the tissue-penetrating arm 110 may be determined based on the tissue with which the tissue repair device 100 is to be used. In some embodiments, the tissue is a body lumen tissue (such as a portion of small or large intestines), and the length of the tissue-penetrating arm 110 is selected to penetrate to the muscular tissue layer M (and, in the case of intestines, through the mucosal MC and submucosal SM layers, as illustrated in FIGS. 3A-3E) from within the lumen, and not to puncture or go through lumen wall to extend to outside the lumen (or organ).

The tissue-grasping arm 120 is movable with respect to the tissue-penetrating arm 110 to provide the tissue-penetrating arm 110 with sufficient space to penetrate tissue near or adjacent the treatment site TS to be repaired without interference by the tissue-grasping arm 120. When the tissue-grasping arm 120 is pivoted away from the tissue-penetrating arm 110 with the tissue-grasping arm 120 substantially axially oriented, the tissue-penetrating arm 110 is not impeded by the tissue-grasping arm 120 of the tissue repair device 100 from penetrating tissue. However, it will be appreciated that in accordance with various principles of the present disclosure, the tissue-grasping arm 120 may limit the extent to which the tissue-penetrating arm 110 may extend through tissue. For instance, once the tissue-penetrating arm 110 has been extended towards the proximal end 113 of the tissue-penetrating arm 110, a proximal region 123 of the tissue-grasping arm 120 comes in contact with an area surrounding the penetration site of the tissue-penetrating arm 110 to inhibit further advancement of the tissue-penetrating arm 110. More particularly, the tissue-grasping arm 120 contacts the surface of the tissue initially contacted by the tissue-penetrating arm 110 before penetrating therethrough. In the context of a tissue repair device 100 used within a body lumen tissue, such initially-contacted tissue would be the inner surface of the lumen tissue; such initially-contacted surface being referenced herein as simply the "surface" of the tissue for the sake of convenience and without intent to limit.

The tissue-grasping arm 120 may have a distal end 121 with one or more hooks 122 configured to grasp tissue. In some embodiments, the hooks 122 are configured to present a substantially blunt distal end 121 to the treatment site TS. As such, the distal end 121 of a tissue-grasping arm 120 with tissue-grasping hooks 122 may serve to limit the insertion of the tissue-penetrating arm 110 through the tissue by contacting the surface of the tissue. The tissue-grasping hooks 122 may be spaced apart so that the tissue-penetrating arm 110 may fit between the tissue-grasping hooks 122 to result in a compact configuration during delivery (e.g., within the flexible elongate member 1010, and/or the shaft 130, and/or the capsule 140).

An example of a manner in which a tissue-repair system 1000 formed in accordance with various principles of the present disclosure is illustrated in FIGS. 3A-3E. As described above, and as illustrated in FIG. 3A, the tissue-penetrating arm 110 may be advanced distally from the shaft 130 and capsule 140 (if included) and into tissue T at the treatment site TS. The tissue-penetrating arm 110 may be advanced through the mucosal layer MC and the submucosal layer SM and into the muscular tissue layer M, as illustrated. If extended too far, the tissue-grasping arm 120 will contact the tissue surface and inhibit further advancement of the tissue-penetrating arm 110 into the tissue.

Figure 3B:
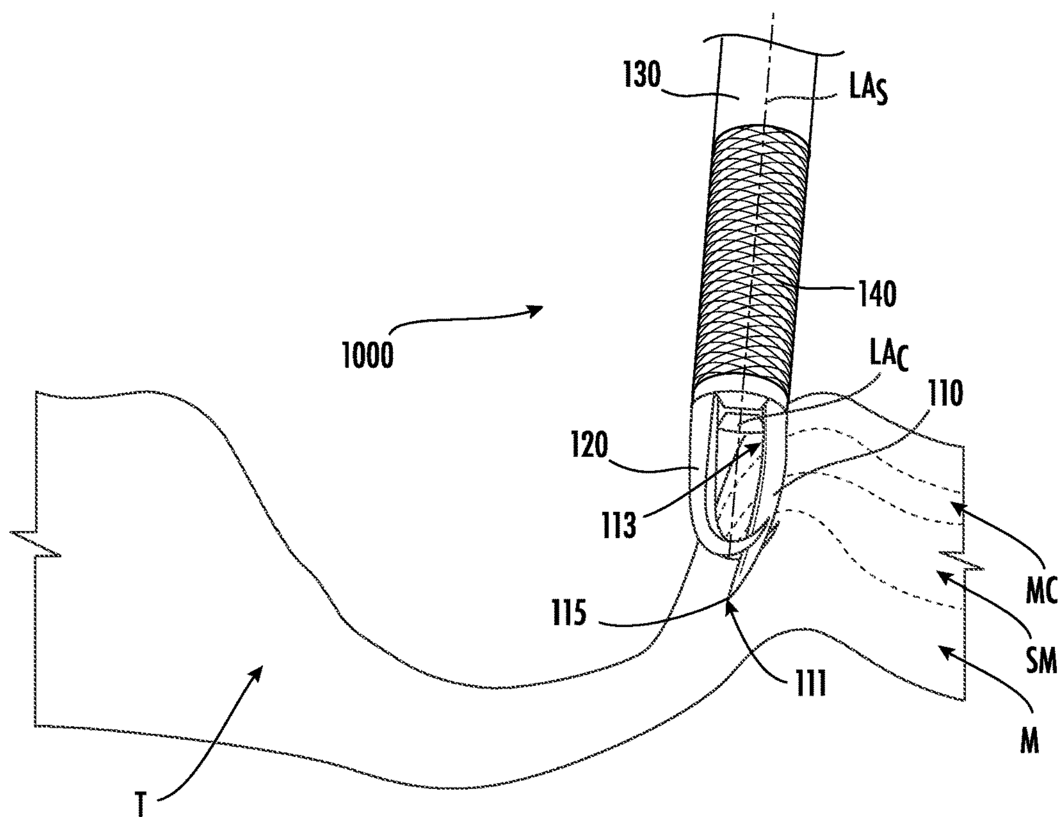

As illustrated in FIG. 3B, once the tissue-penetrating arm 110 is sufficiently advanced, the tissue-grasping arm 120 is brought closer to the tissue-penetrating arm 110 (such as by proximally withdrawing the tissue-penetrating arm 110 and tissue-grasping arm 120 into the shaft 130/capsule 140) to close the tissue repair device 100. The initial tissue at the anchoring location, at which the tissue-penetrating arm 110 is advanced or anchored, is thereby grasped by the tissue-grasping arm 120, and, generally, by the tissue repair device 100. The tissue repair device 100 may then be moved or pulled to another location (which may be referenced herein as a repair location for the sake of convenience and without intent to limit) along the treatment site TS (e.g., along the tissue defect) to repair the defect.

Figure 3C:
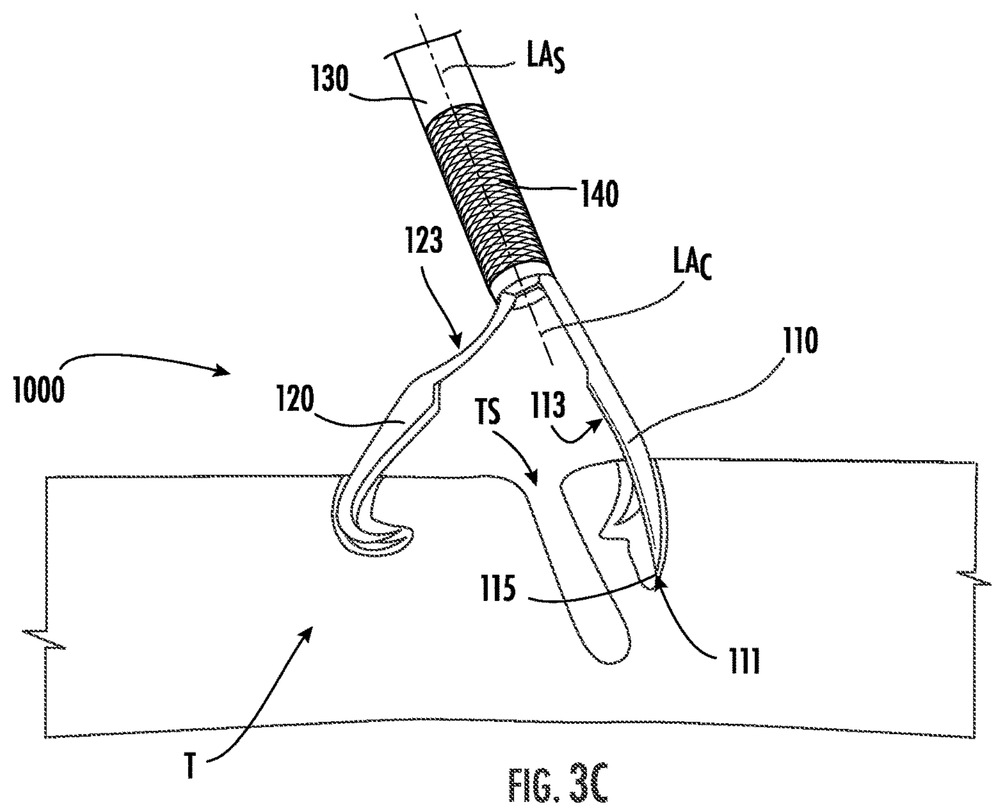

Once at a repair location, as illustrated in FIG. 3C, the tissue repair device 100 may be returned to an open configuration with the tissue-grasping arm 120 positioned away from the tissue-penetrating arm 110 to grasp tissue at the repair location. The tissue-grasping hooks 122 at the distal end 121 of the tissue-grasping arm 120, if provided, may be used to grab tissue at the tissue repair site while the tissue-penetrating arm 110 retains the initial tissue at the anchoring location. In the illustrated embodiment, the tissue-grasping hook 122 extend from a side or surface of the tissue-grasping arm 120 facing the tissue-penetrating arm 110 in a direction towards the tissue-penetrating arm 110. At least one hook 112 may be provided on the tissue-penetrating arm 110 extending transverse to (e.g., perpendicular or otherwise angled) the axial extent of the tissue-penetrating arm 110. In some embodiments, the tissue-penetrating arm hook 112 is positioned proximally spaced from the distal end 111 of the tissue-penetrating arm 110. The tissue-penetrating hook 112 may be used to assist in retaining the initially-grasped tissue (at the first position) in engagement with the tissue repair device 100 and in maintaining the position of the tissue-penetrating arm 110 in place within the anchoring location. The tissue-penetrating hooks 112 may be shaped and configured to retain tissue relative to the tissue-penetrating arm 110 or to retain the tissue-penetrating arm 110 in place in tissue when the tissue-grasping arm 120 is moved laterally (such as in a direction away from the tissue-penetrating arm 110) and/or when the tissue-penetrating arm 110 is moved laterally, such as to move the grasper arms 110, 120 to another position with respect to the treatment site TS.

Figure 3D:
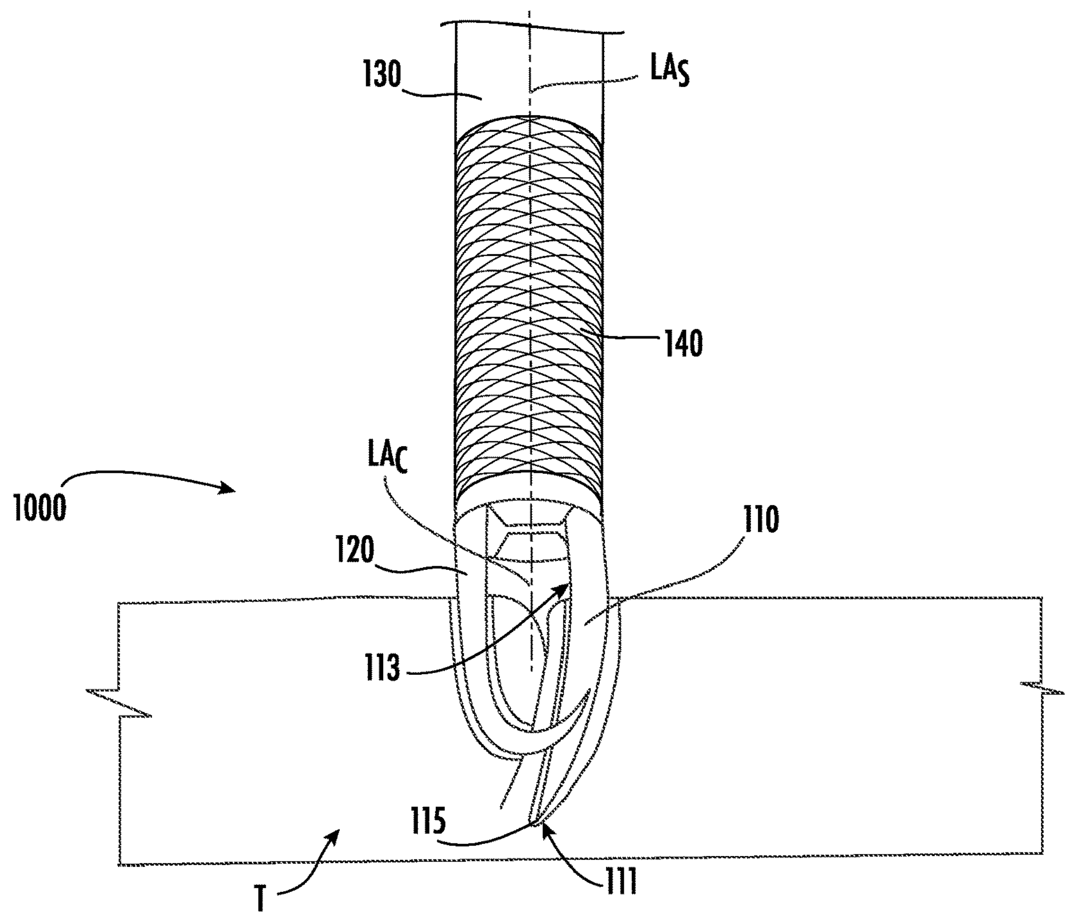
Figure 3E:
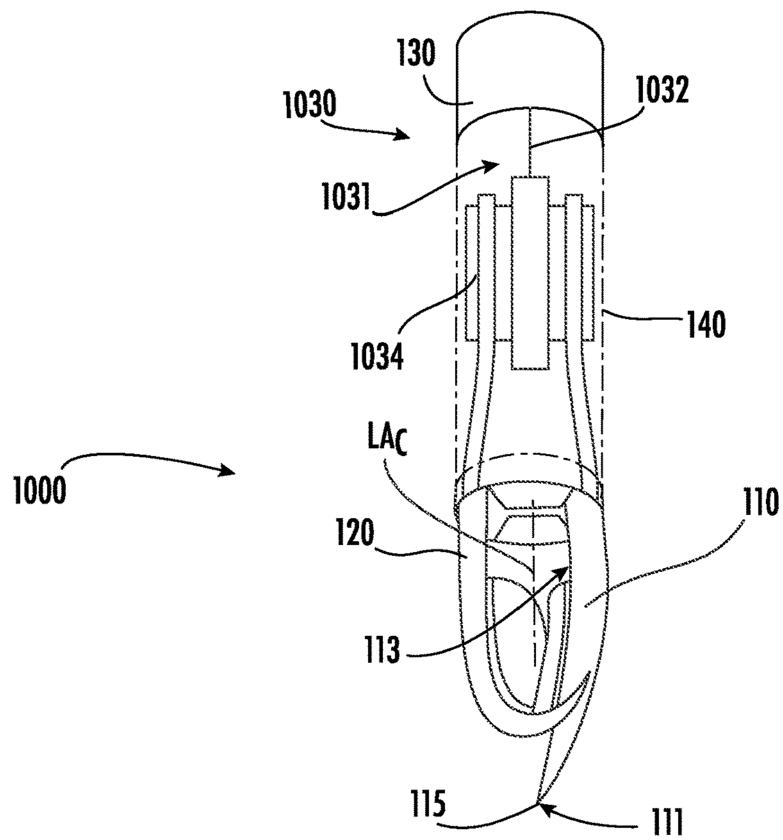
Figure 7A:
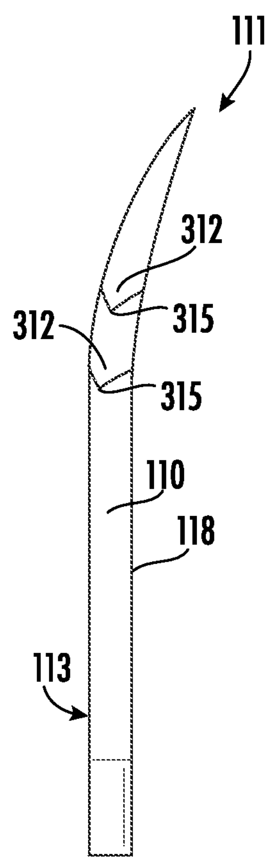
FIGS. 7A and 7B show an isolated side and front elevational view, respectively, of an alternate embodiment of a tissue-penetrating arm in accordance with various principles of the present disclosure.
Figure 7B:
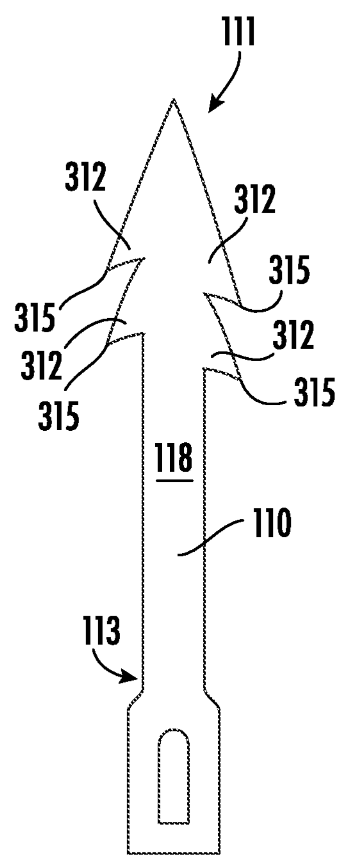

As illustrated in FIG. 3D, once tissue T is grasped by the tissue-grasping arm 120 (e.g., at the desired location, in a sufficient amount, etc.) at the repair location, the tissue repair device 100 may be returned to a closed configuration by bringing the tissue-grasping arm 120 closer to the tissue-penetrating arm 110 (such as by proximally withdrawing the tissue-penetrating arm 110 and tissue-grasping arm 120 into the shaft 130/capsule 140) to close the tissue repair device 100. Further procedures, as medically indicated, may now be performed at or near the treatment site TS.

As illustrated in FIG. 3E, the tissue repair device 100 optionally may be left in place, such as by locking the tissue-penetrating arm 110 and the tissue-grasping arm 120 in a closed configuration and separating the tissue repair device 100 from the tissue-repair system 1000 (e.g., the flexible elongate member 1010) to maintain closure of the defect. In some embodiments, the capsule 140 is separable from the flexible elongate member 1010 such that the grasper arms 110, 120 remain held in a closed configuration (e.g., grasping tissue) by the capsule 140 and the flexible elongate member 1010 is withdrawn therefrom.

In some embodiments, the above-described movements of the tissue-penetrating arm 110 and the tissue-grasping arm 120 are achieved via the above-mentioned tissue-repair device controller 1030. Further details of the interactions of the grasper arms 110, 120 and the tissue repair device controller 1030 may be appreciated with reference to FIG. 3E, showing the capsule 140 in phantom. A distal end 1031 of the tissue-repair device controller 1030 is coupled to the grasper arms 110, 120, such as via a control element 1032 (such as a wire or shaft or other component or structure known or heretofore known in the art capable of moving the grasper arms 110, 120 with respect to the shaft 130 and/or capsule 140). The tissue-repair device controller 1030 may be moved proximally to draw the grasper arms 110, 120 into the flexible elongate member 1010, and/or the shaft 130, and/or the capsule 140 and thereby move the tissue-grasping arm 120 closer to the tissue-penetrating arm 110. The tissue-repair device controller 1030 is selectively separably coupled to the tissue repair device 100 by a connection which allows selective separation of the tissue-repair device controller 1030 from the tissue repair device 100 upon application of a separation force. Various configurations of such connection may be used in conjunction with the tissue repair device 100 of the present disclosure, such as disclosed in U.S. Pat. No. 7,494,461, issued Feb. 24, 2009, to Wells et al., and titled “THROUGH THE SCOPE TENSION MEMBER RELEASE CLIP”; U.S. Pat. No. 8,080,021, issued Dec. 20, 2011, to Griego, and titled “MULTIPLE CLIP DEPLOYMENT MAGAZINE”; and U.S. Pat. No. 8,162,959, issued Apr. 24, 2012, to Cohen et al., and titled “SINGLE STAGE HEMOSTASIS CLIPPING DEVICE”, all of which patents are incorporated by referenced herein in their entireties for all purposes. In one example, as illustrated in FIG. 4E, the tissue-repair device controller 1030 is coupled to the grasper arms 110, 120 with a controller coupling 1034 (such term being used herein for the sake of convenience and may used interchangeably herein with such terms as a bushing, yoke, collar, holder, etc., without intent to limit) known or heretofore in the art, configured to transmit the desired control movements or actions from the tissue-repair device controller 1030 to the grasper arms 110, 120. The controller coupling 1034 preferably holds the proximal ends 113, 123 of the grasper arms 110, 120 in place while allowing flexing or other movement (e.g., radially outward movement or expansion) of the grasper arms 110, 120. The controller coupling 1034 may seat inside windows or cut-outs or grooves within the shaft 130 or the capsule 140 to inhibit or to lock the grasper arms 110, 120 in a desired configuration. An additional projection or stop within the shaft 130 or the capsule 140, or adjacent a proximal end 143 of the capsule 140 may be provided to create a hard stop for the controller coupling 1034. Other configurations, such as bayonet locks or barbs other elements, are within the scope of the present disclosure. Once the grasper arms 110, 120 have been moved into a desired closed configuration (e.g., grasping tissue), the control element 1032 coupled to the grasper arms 110, 120 may be moved proximally with sufficient separation force to detach the control element 1032 from the grasper arms 110, 120, such as via a frangible or breakable or otherwise weakened connection therebetween, as disclosed in the above-incorporated patents. For instance, the control element 1032 may have a weakened area (optionally proximal to a distalmost end at which the control element 1032 is secured to the grasper arms 110, 120) which breaks or otherwise disconnects upon application of the separation force thereto. Additionally or alternatively, frictional forces or specific geometries (interengaging) of the grasper arms 110, 120 and the controller coupling 1034 and/or the shaft 130 and/or the capsule 140 may cause desired binding of the tissue-repair system 1000 to hold the grasper arms 110, 120 in the desired place or configuration. Additionally or alternatively, frictional forces or specific geometries (interengaging) of the grasper arms 110, 120 and the controller coupling 1034 and/or the shaft 130 and/or the capsule 140 may cause desired binding of the tissue-repair system 1000 to hold the grasper arms 110, 120 in the desired place or configuration. It will be appreciated that other configurations of a tissue-repair device controller and a controller coupling are within the scope and spirit of the present disclosure, operation and movement of the grasper arms not being limited by a particular configuration of controller or controller coupling.

It will be appreciated that various modifications to the shape and configuration of the grasper arms 110, 120 may be made without departing from the scope and spirit of the present disclosure. For instance, FIGS. 4A, 4B, 5A, 5B, 6A, 6B show various modifications to the one or more hooks 112 on the tissue-penetrating arm 110 illustrated in the embodiment of FIGS. 2A, 2B, 3A-3E. As noted above, one or more tissue-penetrating hooks 112 may be provided on the tissue-penetrating arm 110—a single hook 112 being illustrated in the embodiment of FIGS. 2A, 2B, 3A-3E, and two tissue-penetrating hooks 112 being illustrated in the embodiment of FIGS. 4A and 4B. The hooks 112 may be sufficiently sharp to help retain tissue when the tissue repair device 100 is pulled to another location along the treatment site TS (e.g., defect).

Alternatively or additionally, the angle of the tissue-penetrating hooks 112 with respect to the shaft longitudinal axis $LA_S$ and/or the capsule longitudinal axis $LA_C$ may be varied. In the examples of embodiments illustrated in FIGS. 2A, 2B, 3A-3E, 4A, 4B, the distal tips 115 (e.g., free ends unconnected to another element) of the tissue-penetrating hooks 112 are directed distally away from the shaft 130/capsule 140. The tissue-penetrating hooks 112 may be at an obtuse angle with respect to the proximal region 113 of the tissue-penetrating arm 110 proximal thereto. In contrast, in the example of an embodiment illustrated in FIG. 5A and FIG. 5B, a tissue-penetrating hook 212 may be provided with a distal tip 215 directed proximally toward the proximal region 113 of the tissue-penetrating arm 110. The tissue-penetrating hooks 212 may be at an acute angle with respect to the proximal region 113 of the tissue-penetrating arm 110 proximal thereto. The distal tips 215 of the tissue-penetrating hooks 212 may be sharp. Additionally or alternatively, the side edges 216 are optionally sharp as well.

Instead of being positioned on the wider side surface 118 of the tissue-penetrating arm 110 (facing the tissue-grasping arm 120 of the tissue repair device 100), as illustrated in FIGS. 2, 3A-3E, 4A-4F, 5A, and 5B, one or more tissue-penetrating hooks 312 with distal tips 317 facing proximally may be provided on the side edges 118 of the tissue-penetrating arm 110, as illustrated in FIG. 6A, FIG. 6B, FIG. 7A, and FIG. 7B. In the illustrated examples of embodiments, two tissue-penetrating hooks 312 are illustrated, though a single hook 312 or more than two hooks 312 may be provided. In the embodiment of FIG. 6A and FIG. 6B, the tissue-penetrating hooks 312 are substantially parallel to or aligned with one another, whereas in the embodiment of FIG. 7A, and FIG. 7B the tissue-penetrating hooks 312 are offset from one another in a direction along the shaft longitudinal axis $LA_S$ and/or the capsule longitudinal axis $LA_C$.

It will be appreciated that further variations to the shape and/or configuration of the tissue-penetrating hooks 112, such as curvature (straight or curved hooks) are within the scope and spirit of the present disclosure. The tissue-penetrating arm 110 may include one or more differently configured tissue-penetrating hooks 112 without departing from the scope and spirit of the present disclosure.

The devices, instruments, tools, etc. of the present disclosure are not limited, and may include a variety of medical devices for accessing and grasping body tissue. The access may be through body passageways, such as via duodenoscopes, catheters, ureteroscopes, bronchoscopes, colonoscopes, arthroscopes, cystoscopes, hysteroscopes, and the like, though may not be so limited. The grasping of tissue may be to repair a defect in the tissue or to perform a procedure on the tissue surrounding the grasped tissue or otherwise.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

It will be appreciated features described with respect to one embodiment typically may be applied to another embodiment, whether or not explicitly indicated. The various features hereinafter described may be used singly or in any combination thereof. Therefore, the present invention is not limited to only the embodiments specifically described herein.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases “at least one”, “one or more”, and “and/or”, as used herein, are open-ended expressions that are both conjunctive and disjunctive in operation. The terms “a”, “an”, “the”, “first”, “second”, etc., do not preclude a plurality. For example, the term “a” or “an” entity, as used herein, refers to one or more of that entity. As such, the terms “a” (or “an”), “one or more” and “at least one” can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader’s understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A tissue repair device comprising:

a tubular component having a longitudinal axis and a lumen defined therein; and a tissue-penetrating arm and a tissue-grasping arm extendable together from a closed position extending laterally adjacent each other within the lumen of the tubular component to a position outside the lumen of the tubular component;

wherein:

the tissue-penetrating arm is shaped and configured to be maintained and to remain in a substantially axially straight configuration from a proximal end thereof to a distalmost end thereof and in a position substantially parallel to the tubular component longitudinal axis when extended to a position outside the tubular component lumen with a tissue-penetrating distal tip of the tissue-penetrating arm extending parallel to the longitudinal axis to be directed axially and distally away from the tubular component to axially penetrate tissue upon distal advancement of the tissue-penetrating arm along the longitudinal axis and toward tissue; and the tissue-grasping arm is pivotable with respect to the tubular component longitudinal axis toward the tissue-penetrating arm to grasp tissue between the tissue-grasping arm and the tissue-penetrating arm, or away from the tissue-penetrating arm, wherein the tissue-grasping arm has a proximal end coupled to the proximal end of the tissue-penetrating arm.

2. The tissue repair device of claim 1, wherein the tissue-grasping arm is biased to move away from the tissue-penetrating arm when extended to a position outside the tubular component lumen, wherein the tissue-penetrating arm and the tissue-grasping arm are in a closed configuration while within the tubular component lumen and in an open position when extended to a position outside the tubular component lumen.

3. The tissue repair device of claim 1, wherein the tissue-penetrating arm includes a sharp axially extending distalmost edge or tip configured to penetrate into tissue.

4. The tissue repair device of claim 3, wherein the tissue-penetrating arm has a length sufficient to penetrate through mucosal, submucosal, and muscular layers of a small intestine without penetrating through a wall of the small intestine.

5. The tissue repair device of claim 4, wherein the tissue-grasping arm has a blunt distal end.

6. The tissue repair device of claim 3, wherein the tissue-grasping arm is configured to inhibit a depth to which the tissue-penetrating arm may penetrate into tissue.

7. The tissue repair device of claim 3, wherein the tissue-penetrating arm comprises a sharp distalmost end extending along the longitudinal axis, and a tissue-penetrating hook positioned proximal to the sharp distalmost end.

8. The tissue repair device of claim 7, wherein the tissue-penetrating hook extends transverse to the tubular component longitudinal axis.

9. The tissue repair device of claim 8, wherein the tissue-penetrating hook is shaped and configured to retain tissue when the tissue-penetrating arm is moved laterally.

10. The tissue repair device of claim 1, wherein the tissue-grasping arm includes at least one tissue-grasping hook.

11. The tissue repair device of claim 1, wherein the tissue-penetrating arm and the tissue-grasping arm are coupled to a control element, and the tissue-penetrating arm is coupled with the control element to be maintained in the position substantially parallel to the tubular component when extended to a position outside the tubular component lumen.

12. The tissue repair device of claim 1, wherein the tissue-grasping hook includes a pair of tissue-grasping hooks facing toward the tissue-penetrating arm, and the tissue-penetrating arm fits between the tissue-grasping hooks when the tissue-grasping arm is moved toward the tissue-penetrating arm.

13. The tissue repair device of claim 10, wherein the tissue-penetrating arm includes at least one hook shaped and configured to retain tissue when at least one of tissue-grasping arm or the tissue-penetrating arm is moved laterally.

14. A tissue repair system comprising:

a flexible elongate member having a lumen defined therein, and a longitudinal axis extending between a distal end of the flexible elongate member and a proximal end of the flexible elongate member;

a tissue-penetrating arm and a tissue-grasping arm extendable from within the flexible elongate member lumen to a position outside the flexible elongate member lumen, wherein the tissue-grasping arm is pivotable to a position toward the tissue-penetrating arm to grasp tissue between the tissue-grasping arm and the tissue-penetrating arm and to a position away from the tissue-penetrating arm;

a controller having a proximal end and a distal end, the controller distal end coupled to a proximal end of the tissue-penetrating arm and a proximal end of the tissue-grasping arm to move the tissue-penetrating arm and the tissue-grasping arm together between a position within the flexible elongate member lumen and a position distally outside the flexible elongate member lumen; and a control handle coupled with the proximal end of the flexible elongate member and the controller to control movement thereof;

wherein:

the tissue-penetrating arm and the tissue-grasping arm are shaped and configured differently from each other, with the pivotable tissue-grasping arm being shorter than the tissue-penetrating arm.

15. The tissue-repair system of claim 14, wherein the tissue-penetrating arm is maintained in a position substantially parallel to the flexible elongate member longitudinal axis when extended to outside the flexible elongate member lumen, and the pivotable tissue-grasping arm is pivotable with respect to the flexible elongate member longitudinal axis toward or away from the tissue-penetrating arm.

16. The tissue-repair system of claim 14, further comprises a capsule coupled to the distal end of the flexible elongate member and defining a lumen therethrough, the tissue-penetrating arm and the tissue-grasping arm movable between a closed configuration within the capsule and an open configuration outside the capsule.

17. The tissue-repair system of claim 16, wherein the capsule is separable from the flexible elongate member with the tissue-penetrating arm and the tissue-grasping arm positioned therein in a closed position.

* * * * *